US006661456B1

(12) United States Patent
Aufrichtig et al.

(10) Patent No.: US 6,661,456 B1
(45) Date of Patent: Dec. 9, 2003

(54) IMAGING OF PIXEL DEFECTS IN DIGITAL DETECTORS

(75) Inventors: Richard Aufrichtig, Mountain View, CA (US); Robert Forrest Kwasnick, Palo Alto, CA (US); John R. Lamberty, Oconomowoc, WI (US); John C. French, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/303,190

(22) Filed: Apr. 30, 1999

(51) Int. Cl.[7] .............................. H04N 9/64; H05G 1/64; A61B 5/05; A61B 6/00
(52) U.S. Cl. .................. 348/247; 378/98.8; 378/98.11; 378/98.12; 378/4; 600/425
(58) Field of Search ................................ 348/246, 247; 378/98, 98.2–98.12, 62, 87, 116, 164, 4, 19, 207; 250/208.1, 370.09; 600/407, 425

(56) References Cited

U.S. PATENT DOCUMENTS

| 5,047,863 A | 9/1991 | Pape et al. ............. 358/213.16 |
| 5,272,536 A | 12/1993 | Sudo et al. ............. 358/213.15 |
| 5,657,400 A | 8/1997 | Granfors et al. ............ 382/254 |
| 5,854,655 A | 12/1998 | Watanabe et al. ........... 348/247 |

*Primary Examiner*—Andrew Christensen
*Assistant Examiner*—Nhan Tran
(74) *Attorney, Agent, or Firm*—Foley & Lardner

(57) ABSTRACT

A method and apparatus for displaying an image generated by at least one detector of an imaging unit are disclosed herein. The method includes creating a pixel map identifying locations of bad pixels in an array of pixels in the image detected by the at least one detector, linking the pixel map to the image, and providing for selective display of the pixel map. Bad pixels behave from a group including pixels which do not respond electrically and pixels which are statistically different from surrounding pixels in the array of pixels. The apparatus includes an imaging unit for generating x-rays which pass through a body of interest, at least one detector unit for detecting the x-rays, and a processing unit for identifying bad pixels within the detected image.

4 Claims, 7 Drawing Sheets

IMAGING OF PIXEL DEFECTS IN DIGITAL DETECTORS

BACKGROUND OF THE INVENTION

The present invention relates generally to imaging systems. More particularly, the present invention relates to a digital imaging system equipped to detect and display defects contained within the imaging detector.

Imaging systems include systems where images are generated by, x-ray, magnetic resonance imaging (MRI), ultrasound, computerized tomography (CT), or such nuclear medicine techniques as positron emission tomography (PET) or single photon emission computerized tomography (SPECT). In each system, a source of electromagnetic radiation (e.g., x-rays) emits radiation which passes through a body of interest and is detected by some kind of detector. Various structures of various densities in the body of interest absorb the radiation differently, such that the radiation detected by the detector provides information on the structures.

Imaging systems are often used to provide detailed information on structures inside the human body. For example, CT scans of the head are useful for evaluation of head injury and detection of tumor, stroke, or infection. Imaging devices are also useful for the detection of pathologies, or manifestations of diseases such as cancer.

Conventional digital image detectors are, nevertheless, known to lose image information at locations in the detected image which contain a detector defect. These defects are typically called "bad pixels." In general, bad pixels are image elements which either do not respond electrically or have a behavior that is statistically different from surrounding pixels in the detector array.

Generally, detection of bad pixels in an imaging system is accomplished by imaging a standard set of test phantoms, such as flat fields, with predetermined imaging techniques. Depending on the number of bad pixels and their proximity to other bad pixels in the detected image, clusters of bad pixels may result and clinically relevant information may be lost.

Thus, there is a need to alert the user of imaging systems as to the location of bad pixels and/or clusters of bad pixels in the displayed image. Further, there is a need to avoid medical misdiagnosis caused by unawareness of detector defects. Even further, there is a need to provide critical information to algorithms which are used to detect local statistical image variations which may mistakenly quantify detector defects as pathologies.

BRIEF SUMMARY OF THE INVENTION

One embodiment of the invention relates to a method for displaying an image generated by at least one detector of an imaging unit. The method includes creating a pixel map identifying locations of bad pixels in an array of pixels in the image detected by the at least one detector, linking the pixel map to the image, and providing for selective display of the pixel map. Bad pixels include pixels which do not respond electrically and/or pixels which are statistically different from surrounding pixels in the array of pixels.

Another embodiment of the invention relates to an apparatus for displaying an image generated by at least one detector of an imaging unit. The apparatus includes means for creating a pixel map identifying locations of bad pixels in an array of pixels in the image detected by the at least one detector, means for linking the pixel map to the image, and means for providing for selective display of the pixel map. Bad pixels include pixels which do not respond electrically and/or pixels which are statistically different from surrounding pixels in the array of pixels.

Another embodiment of the invention relates to an apparatus for displaying an image. The apparatus includes an imaging unit, at least one detector unit, a processing unit, and a display. The imaging unit generates x-rays which pass through a body of interest having a structure. The at least one detector unit detects the x-rays which pass through the body of interest to form an image. The image includes an array of pixels which contain information on the structure. The processing unit is coupled to the at least one detector unit and identifies bad pixels within the array of pixels in the image formed by the at least one detector unit. Bad pixels include pixels which do not respond electrically and/or pixels which are statistically different from surrounding pixels in an array of pixels. The display is coupled to the processing unit and provides visual display of the image and selectively displays the bad pixels.

Other principle features and advantages of the present invention will become apparent to those skilled in the art upon review of the following drawings, the detailed description, and the appended claims.

BRIEF DESCRIPTION OF THE DRAWINGS

The invention will become more fully understood from the following detailed description, taken in conjunction with the accompanying drawings, wherein like reference numerals denote like elements, in which.

DETAILED DESCRIPTION OF THE INVENTION

Figure 1:
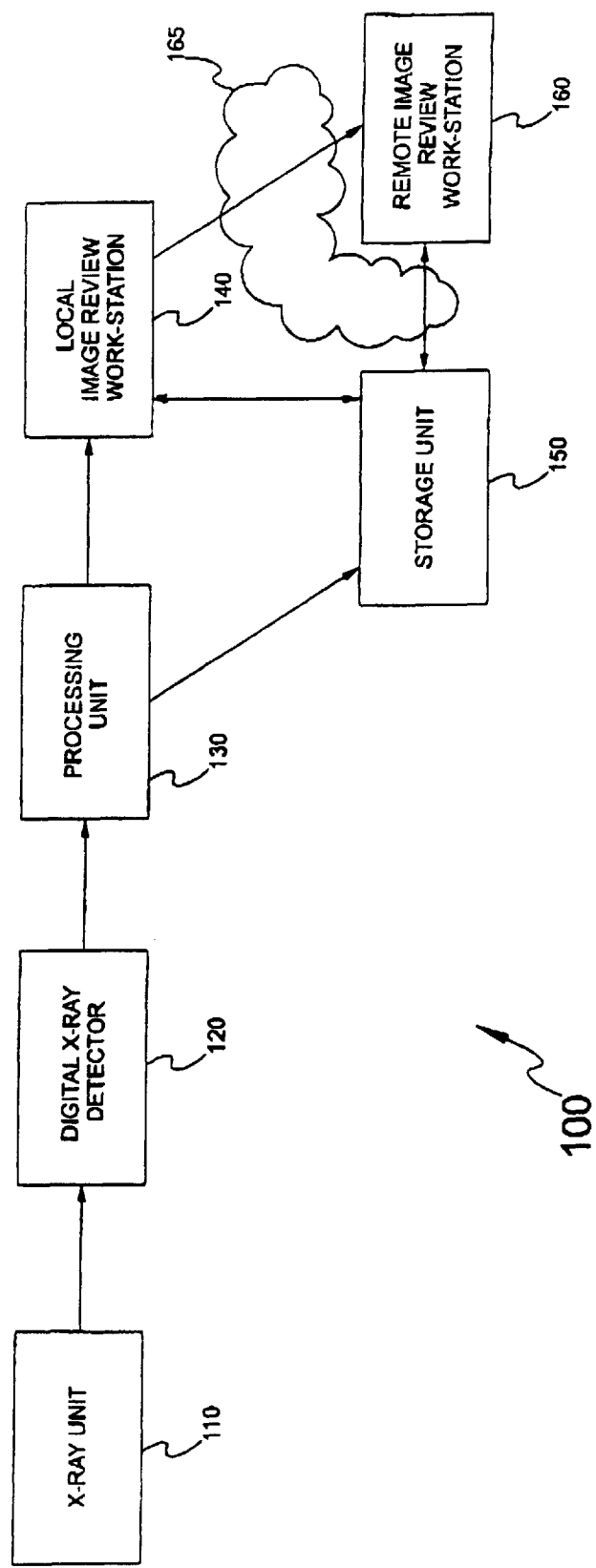
FIG. 1 is a general block diagram of an x-ray imaging system in accordance with the present invention.

FIG. 1 is a general block diagram of an x-ray imaging system 100. System 100 includes an x-ray unit 110, a digital x-ray detector 120, a local computer or processing unit 130, a local image review station 140, a storage unit 150, and a remote image review station 160. X-ray unit 110 is an x-ray generating unit which includes an x-ray generator and x-ray tube. X-ray unit 110 generates x-rays which pass through a body of interest (e.g., part of a human body).

In alternative embodiments, imaging system 100 is any of a variety of imaging systems (e.g., ultrasound). Such alternative embodiments include components characteristic to the particular type of imaging system used.

After passing through the body of interest, the x-rays from x-ray unit 110 are detected by digital x-ray detector 120, which forms an image from the x-rays. The image detected by detector 120 includes an array of pixels, or image elements, which contain information on the detected x-rays and, thus, of the structures within the body of interest. Detector 120 includes electronics for communicating data on the x-rays to other devices.

Processing unit 130 is any of a variety of programmable electronic machines which performs operations or assembles, stores, correlates, or otherwise processes information. In one embodiment, processing unit 130 is a computer. Processing unit 130 processes the x-ray data from detector 120. Processing unit 130 is coupled to detector 120 and identifies bad pixels within the array of pixels in the image detected by detector 120. Bad pixels are pixels that either do not respond electronically or are statistically different from surrounding pixels in the array of pixels.

Local image review station 140 includes a display and controls. Local image review station 140 is coupled to processing unit 130 and provides graphical and/or textual display of x-ray imaging data from x-ray unit 110 and digital x-ray detector 120. Controls on local image review station 140 allow a reviewer to change a variety of display options. For example, station 140 can be configured by the reviewer to selectively display a map of bad pixels superimposed on the image.

Storage unit 150 is coupled to any one of processing unit 130 and station 140. Storage unit 150 is preferably a disk drive for storing digital information. Storage unit 150 is alternatively a solid state storage device or any other memory component capable of maintaining data displayed on local image review station 140. Further still, storage unit 150 is alternatively integrated into processing unit 130. Storage unit 150 maintains x-ray imaging data in the form of an image file. Thus, x-ray imaging data is available for later retrieval either by local station 140 or remote station 160.

Remote image review station 160 includes a display and controls. Remote image review station 160 is similar to local review station 140 in that station 160 provides graphical and/or textual display of x-ray imaging data from x-ray unit 110. Further, controls allow a reviewer to change a variety of display options. For example, station 160 provides for the selective display of a map of bad pixels. Remote station 160 is coupled to local image review station 140 or storage unit 150 by a network 165. Network 165 is a local area network (LAN), wide area network (WAN), synchronous optical network (SONET), or any other interconnection of electronic components for sharing information.

Station 160 advantageously provides doctors or other trained personnel located remotely from x-ray unit 110 with access to graphical and textual display of x-ray imaging data. Station 160 obtains x-ray imaging data either from local station 140 or from archived copies in storage unit 150.

Alternatively, system 100 includes a plurality of detectors 120, forming an array of detectors. Where an array of detectors is used, one image is obtained from the plurality of detectors. The one image from the plurality of detectors 120 is processed by processing unit 130 and displayed by station 140 or station 160. For example, a CT device includes an array of detectors arranged along the inside perimeter of a slip ring. The one image from the plurality of detectors may include bad pixels in the image due to defects in one or multiple detectors.

Figure 2:
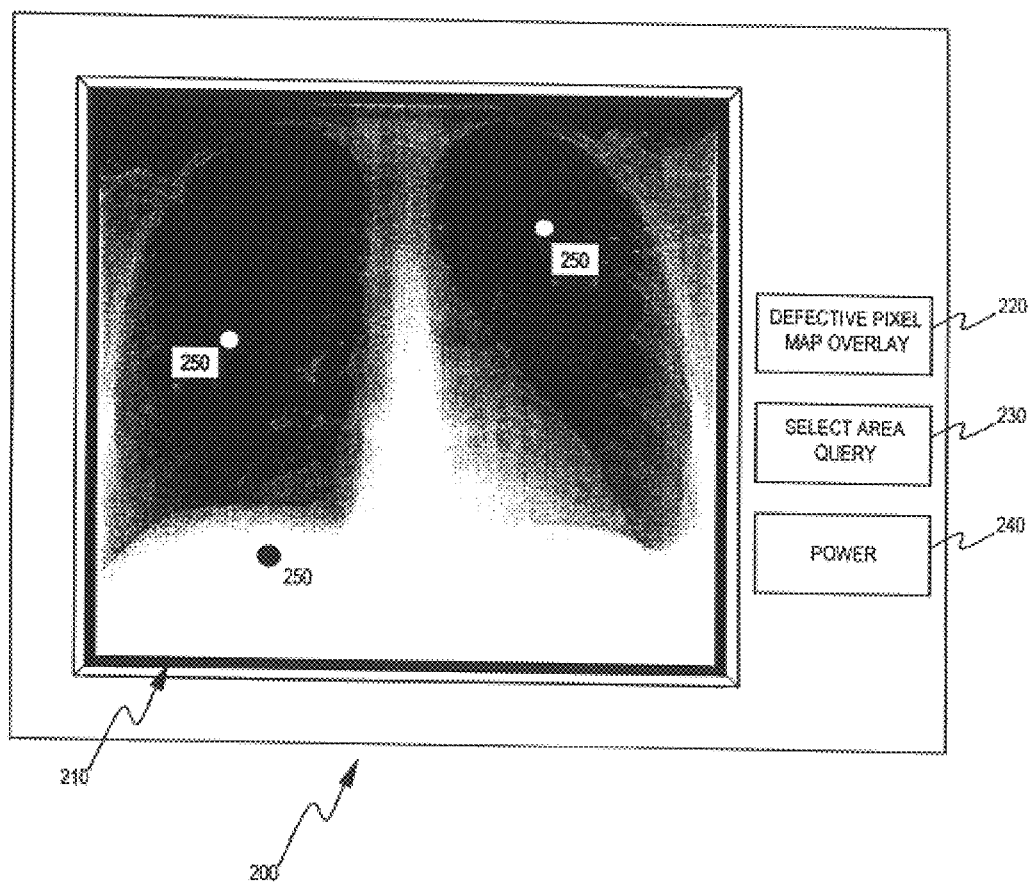
FIG. 2 is a display of an exemplary image in an embodiment of the x-ray detector system of FIG. 1.

In an exemplary embodiment, local image review station 140 and remote image review station 160 each include a display unit 200. FIG. 2 illustrates display unit 200 including a display 210, a defective pixel map overlay control 220, a select area query control 230, and a power switch 240.

Display 210 is a cathode ray tube (CRT) display, thin film transistor (TFT) display, or any other device for displaying images. Display 210 shows an image of a human chest using x-ray unit 110 in a defective pixel map overlay mode. In defective pixel map overlay mode, display unit 200 displays the clinical image of the chest with a defective pixel map overlay. The overlay includes an operator selection of white, black, color-coded, or alternative symbols to identify bad pixel locations. Where color coding is used, different colors characterize different detector defects. A color coding index is available at station 140.

In the embodiment of FIG. 2, display 210 is a black and white display that reveals detector pixel defects 250 in reverse color on the image. For example, where the image on display 210 is white, pixel defects are shown in black and, where the image on display 210 is black, pixel defects are shown in white. The image shown in display 210 (including defective pixels) can be output to a laser printer or other printing device.

Controls 220 and 230 are buttons on display unit 200 which allow the image reviewer to select one of two pixel defect display modes. In the first pixel defect display mode, the image reviewer is shown display 210 with a defective pixel map overlaying the image. In the second pixel defect display mode, the image reviewer is shown display 210 and allowed to select areas on the display in order to query whether those areas contain bad pixels. Controls 220 and 230 are alternatively included as touch-screen buttons on display 210, selections in a menu bar on display 210, or any other arrangement in the user interface of display unit 200. Power switch 240 is an on/off button activating or deactivating display unit 200.

Figure 3:
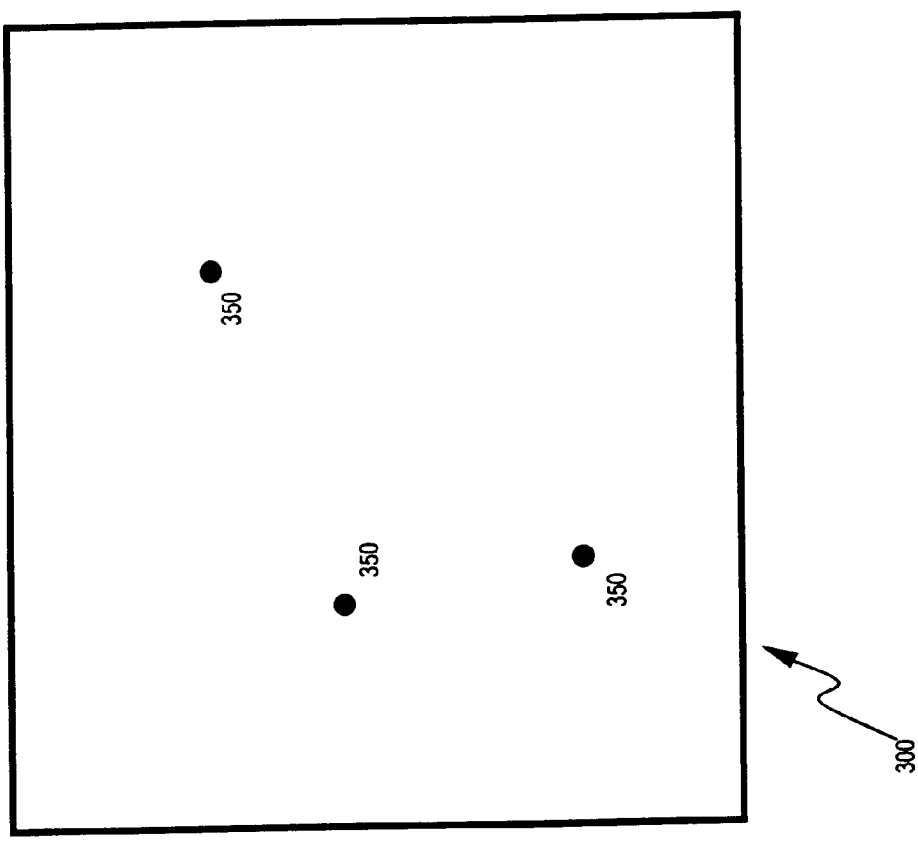
FIG. 3 is a pixel map including detected bad pixels in the displayed image of FIG. 2.

FIG. 3 is a pixel map 300 which can be displayed on display unit 200. Pixel map 300 includes bad pixels 350 within an array of pixels. Bad pixels 350 are identified by processing unit 130 as pixels which either do not respond electronically or behave in a manner which is statistically different from surrounding pixels in the array of pixels. The locations of bad pixels 350 are included in the image file of storage unit 150 as row and column locations in the array of pixels.

Figure 4:
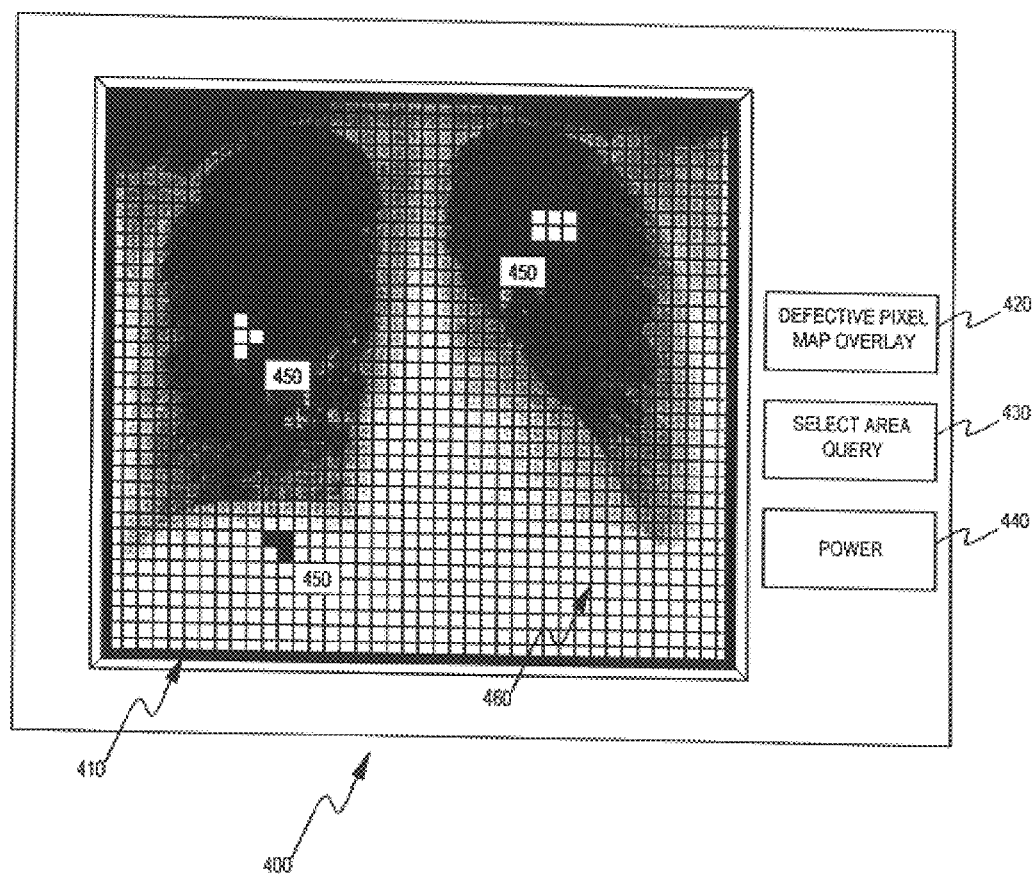
FIG. 4 is the display of FIG. 2 including a grid showing the displayed image divided into an array of pixels.

FIG. 4 illustrates a display unit 400 including a pixel grid 460. Pixel grid 460 is not displayed on display 410, rather it is used in FIG. 4 to illustrate the division of the image displayed by display 410 into an array of pixels. Pixel defects 450 are single bad pixels or clusters of bad pixels in the image. The locations of pixel defects 450 are included in an information header of the image file stored in storage unit 150 as row and column locations.

Figure 5:
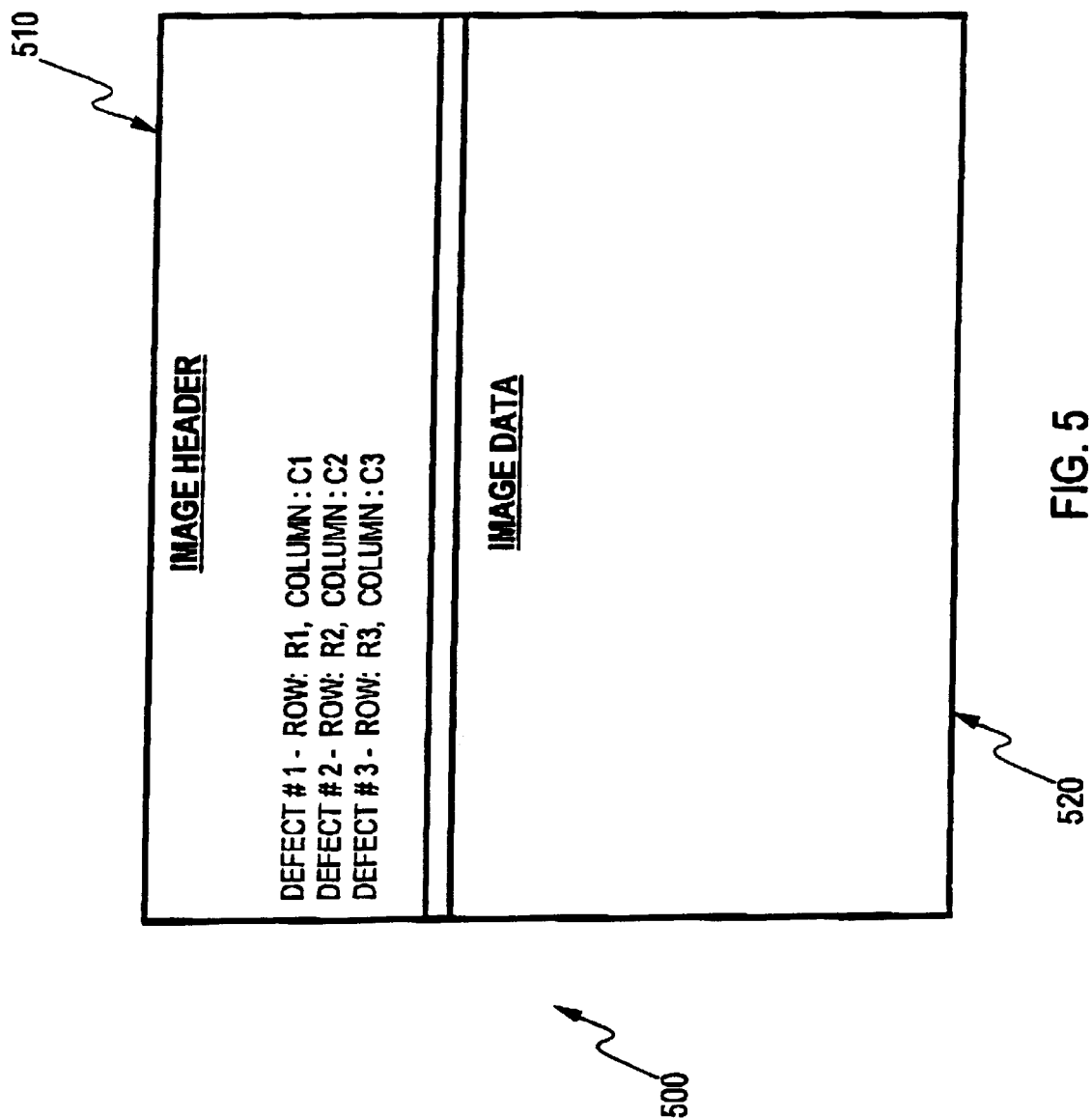
FIG. 5 is a block diagram of a file in a second embodiment of the x-ray detector system of FIG. 1.

FIG. 5 is a block diagram of an exemplary file 500 of x-ray detector system 100. File 500 is a computer file, linked list, array, or any other data structure for arranging and storing information. File 500 includes an image header 510 and image data 520. Image header 510 contains data representative of the locations of detected bad pixels and clusters (e.g., row and column indicia for each defect). Image data 520 contains data representative of the clinical image, such as image data for the human chest of FIG. 2. File 500 is formatted in text, HTML, ASCII, or any of a variety of file formats.

Image header 510 provides a link of bad pixel data to a corresponding image. Linking the bad pixel data with a corresponding image advantageously provides access to reliable image information for both currently displayed images and archived image files.

Figure 6:
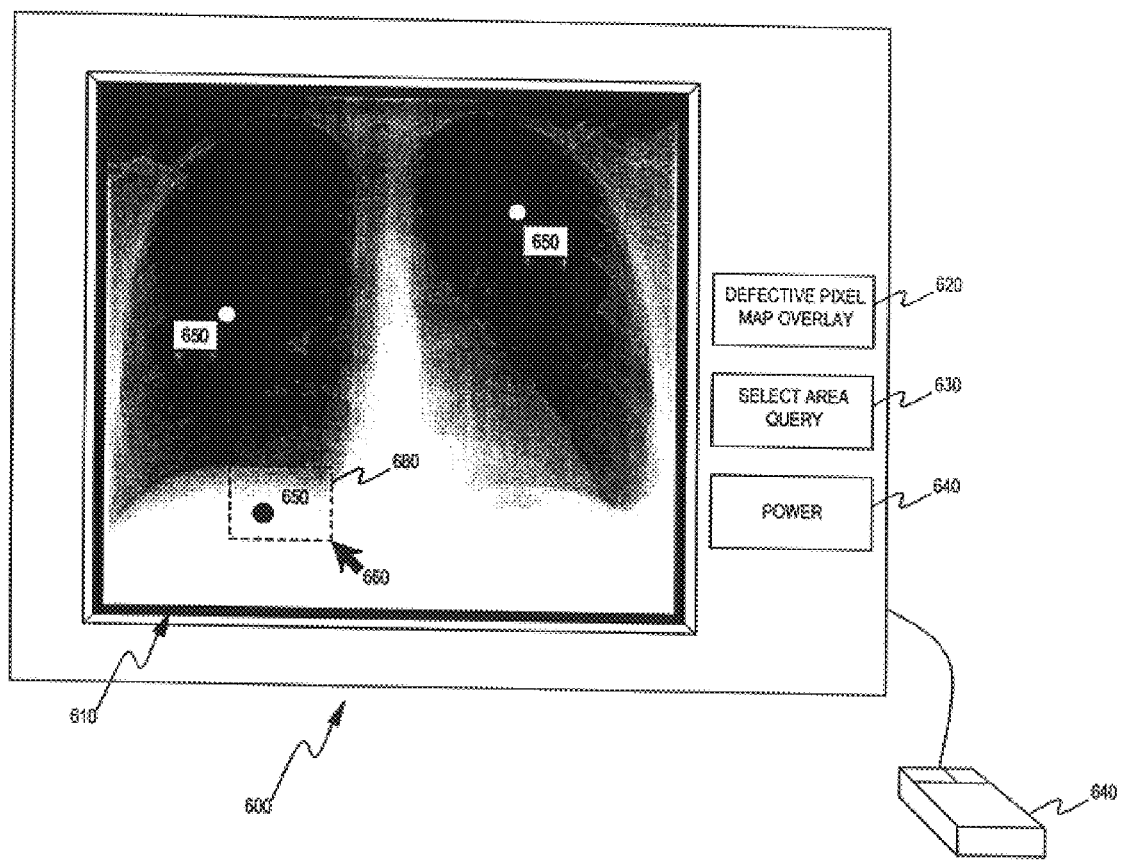
FIG. 6 is a display of an exemplary image in a third embodiment of the x-ray detector system of FIG. 1.

FIG. 6 illustrates a display unit 600 in another embodiment of x-ray detector system 100. Display unit 600 includes a display 610, a defective pixel map overlay control 620, a select area query control 630, and a power switch 640. Display 610, controls 620 and 630, and power switch 640 are substantially the same as display 210, controls 220 and 230, and power switch 240 in FIG. 2.

Display 610 provides a graphical image of a human chest using x-ray unit 110 in a select area query mode. In the select area query mode, a reviewer of the image selects an area using, for example, a mouse cursor 660 controlled by a mouse input device 670. After selection of an area using input device 670, a dashed box 680 is displayed to indicate the particular area selected. Alternatively, the reviewer of the image selects an area on the image by touching the screen at that area, creating a box around the area using a computer mouse, or any of a variety of user interface arrangements.

Once the area in question is selected, display unit 600 displays whether the selected area contains a bad pixel or cluster of bad pixels, such as pixel defects 650, by displaying a graphical area overlay similar to that used in defective pixel map overlay mode (FIG. 2) in the selected area or by giving a graphical or textual indication as to whether a bad pixel is present in the selected area. For example, a text message "NO DEFECTIVE PIXELS IN AREA" is alternatively displayed for selected areas without bad pixels. Display 610 can be output to a laser printer or other printing device.

Figure 7:
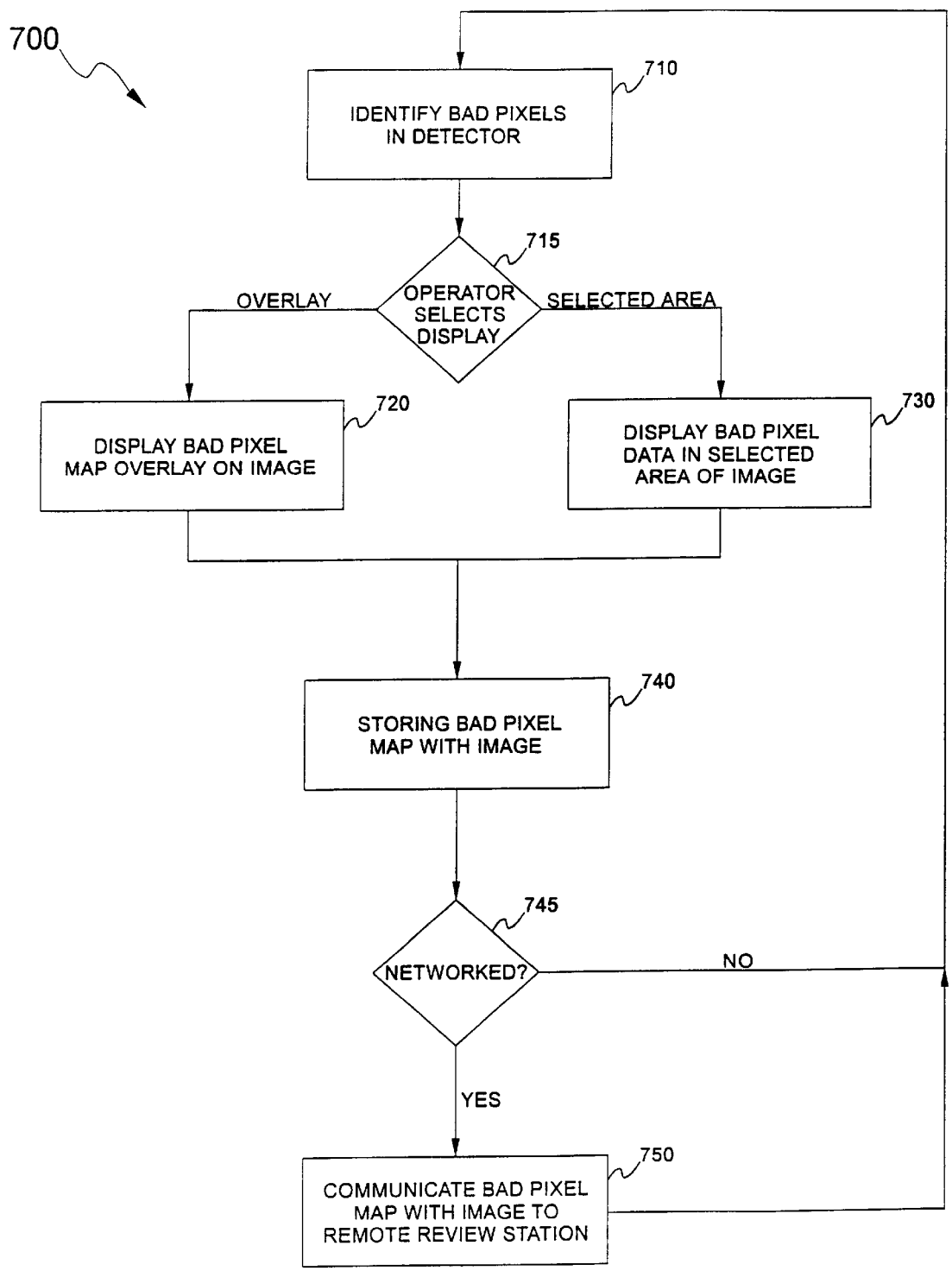
FIG. 7 is a flow chart of an exemplary method used to visualize bad pixels in the image detected by the detector of the system shown in FIG. 1.

FIG. 7 is a flow chart 700 of an exemplary method used to visualize bad pixels in the image detected by detector 120 of x-ray detector system 100. In a step 710, standard imaging techniques are used to identify bad pixels, or image elements, within an array of pixels in the image detected by detector 120. Bad pixels are pixels that either do not respond electrically or have a behavior that is statistically different from surrounding pixels in the array of pixels. A map of the detected bad pixels identified is stored in processing unit 130. Standard imaging techniques for identifying bad pixels include, for example, those disclosed in U.S. Pat. No. 5,657,400 issued to Granfors et al.; U.S. Pat. No. 5,854,655 issued to Watanabe, et al.; U.S. Pat. No. 5,272,536 issued to Sudo et al.; and U.S. Pat. No. 5,047,863 issued to Pape, et al.

After step 710, a step 715 is performed in which the operator of local image review station 140 selects the desired type of bad pixel display. The operator preferably chooses either an overlay display using control 220, 420 or 620 or a selected area display using control 240, 440 or 640. If the operator chooses an overlay display, a step 720 is performed. If the operator chooses a selected area display, a step 730 is performed.

In step 720, the bad pixel map is displayed overlaying the clinical image acquired by detector 120 on local image review station 140. An example of an overlay display is shown in FIG. 2.

In step 730, the operator selects a clinically suspicious area on the clinical image using a mouse cursor, keyboard keys, or other types of controls. A clinically suspicious area may be one which includes lone graphical aberrations in the image, inconsistent patterns in the image, or other image anomalies.

Defects in the selected area are preferably displayed using a graphical overlay for the selected area. An example of a selected area display including mouse cursor 660 is shown in FIG. 6. Further, a text message is alternatively displayed indicating the presence or absence of defective pixels within the selected area. Alternatively, a numerical value representing the quality of the detector in the selected area is displayed. The numerical value represents, for example, the number of bad pixels within the selected area.

After step 720 or 730, a step 740 is performed in which the clinical image of x-ray unit 10 is archived locally onto storage unit 150. A bad pixel map identified by processing unit 130 is included with the clinical image as an information field in the information header of the image file and stored in storage unit 150. An example of an image file is shown in FIG. 5.

As such, header information including the location of bad pixels in the array of pixels displayed is available for advanced imaging algorithms. The algorithms use the location of bad pixel information to avoid mistaking a defect for a clinical pathology or enhancing a defect during manipulation by the algorithm. Advanced imaging algorithms include algorithms for computer assisted diagnosis (CAD) or other digital image enhancement methods.

After step 740, a step 745 is performed to determine if x-ray detector system 100 is networked to remote image review station 160. If so, a step 750 is performed in which the clinical image, including the bad pixel map in the image header, is communicated to remote image review station 160 by network 165. Steps 715, 720, and 730 are performed at remote image review station 160 to provide display of bad pixels in the clinical image in a similar fashion to the display at local review station 140.

X-ray detector system 100 discussed in reference to FIGS. 1–6 and the method discussed with reference to FIG. 7 advantageously provide selective display of bad pixels (and/or clusters of bad pixels) in the image detected by detector 120. Further, system 100 links images from x-ray unit 110 with a map of corresponding bad pixels detected on detector 120 by processing unit 130.

Thus, human reviewers of the image and computer algorithms analyzing the image are provided with information which identifies bad detector pixels. As such, bad pixels are not mistaken for clinical pathologies either by human reviewers or computer programs. Further, bad pixels are not enhanced by CAD algorithms. Therefore, x-ray defector system 100 and systems utilizing the method discussed above are more reliable and more effective imaging systems.

While the embodiments illustrated in the FIGURES and described above are presently preferred, it should be understood that these embodiments are offered by way of example only. Other embodiments may include, for example, data structures other than arrays to contain information from x-ray unit 110. Further, the term pixel should be understood to include any image or picture element. For purposes of the present invention, the use of the term "pixel" may be interpreted to include picture or image elements, and, depending on the application, may represent a voxel or predefined area or volume. "Pixel" should not be limited to a single picture or image element, elements necessarily arranged in a matrix, or an element of a particular size or shape. The invention is not limited to a particular embodiment, but extends to various modifications, combinations, and permutations that nevertheless fall within the scope and spirit of the appended claims.

What is claimed is:

1. A method for displaying an image generated by at least one detector of an imaging unit, the method comprising:
   creating a pixel map identifying locations of bad pixels in an array of pixels in the image detected by the at least one detector, the bad pixels behaving from a group including pixels which do not respond electrically and pixels which are statistically different from surrounding pixels in the array of pixels;

linking the pixel map to the image; and providing for selective display of the pixel map,
- wherein the providing step includes providing a graphical overlay with graphical symbolic representations of the bad pixels superimposed on the image
- and the graphical symbolic representations are a plurality of colors, each color characterizing a different defect.

2. A method for displaying an image generated by at least one detector of an imaging unit, the method comprising:

creating a pixel map identifying locations of bad pixels in an array of pixels in the image detected by the at least one detector, the bad pixels behaving from a group including pixels which do not respond electrically and pixels which are statistically different from surrounding pixels in the array of pixels;

linking the pixel map to the image; and providing for selective display of the pixel map,
- wherein the providing step includes providing a graphical overlay with graphical symbolic representations of the bad pixels superimposed on the image wherein the graphical symbolic representations are a plurality of colors, each color characterizing a different defect; and
- wherein the graphical symbolic representations reveal bad pixels in reverse color of the image.

3. An apparatus for displaying an image generated by at least one detector of an imaging unit, the apparatus comprising:

means for creating a pixel map identifying locations of bad pixels in an array of pixels in the image detected by the at least one detector, the bad pixels behaving from a group including pixels which do not respond electrically and pixels which are statistically different from surrounding pixels in the array of pixels;

means for linking the pixel map to the image; and means for providing for selective display of the pixel map
- wherein the means for providing includes means for providing graphical symbolic representations of the bad pixels superimposed on the image;
- wherein the graphical symbolic representations are a plurality of colors, each color characterizing a different defect.

4. An apparatus for displaying an image, the apparatus comprising:

an imaging unit for generating x-rays which pass through a body of interest having a structure;

at least one detector unit for detecting the x-rays which pass through the body of interest to form an image, the image including an array of pixels which contain information on the structure;

a processing unit coupled to the at least one detector unit, the processing unit configured to identify bad pixels within the array of pixels in the image formed by the at least one detector unit, the bad pixels behaving from a group including pixels which do not respond electrically and pixels which are statistically different from surrounding pixels in the array of pixels; and a display coupled to the processing unit and providing visual display of the image and selectively displaying the bad pixels, wherein the display selectively displays the bad pixels by providing a graphical overlay with graphical symbolic representations of the bad pixels superimposed on the image,
- wherein the graphical symbolic representations are a plurality of colors, each color characterizing a different defect.

* * * * *